United States Patent
Tirtowidjojo et al.

(10) Patent No.: US 9,512,049 B2
(45) Date of Patent: Dec. 6, 2016

(54) PROCESS FOR THE PRODUCTION OF ALKENES AND/OR AROMATIC COMPOUNDS

(71) Applicant: DOW GLOBAL TECHNOLOGIES LLC, Midland, MI (US)

(72) Inventors: Max Markus Tirtowidjojo, Lake Jackson, TX (US); Brien A. Stears, League City, TX (US); William J. Kruper, Jr., Sanford, MI (US); Kurt F. Hirsekorn, Midland, MI (US); Debashis Chakraborty, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 365 days.

(21) Appl. No.: 14/367,542

(22) PCT Filed: Dec. 21, 2012

(86) PCT No.: PCT/US2012/071102
§ 371 (c)(1),
(2) Date: Jun. 20, 2014

(87) PCT Pub. No.: WO2013/096706
PCT Pub. Date: Jun. 27, 2013

(65) Prior Publication Data
US 2014/0336431 A1    Nov. 13, 2014

Related U.S. Application Data

(60) Provisional application No. 61/579,777, filed on Dec. 23, 2011.

(51) Int. Cl.
*C07C 2/86* (2006.01)

(52) U.S. Cl.
CPC ........... *C07C 2/861* (2013.01); *C07C 2531/02* (2013.01)

(58) Field of Classification Search
CPC ..................................................... C07C 2/861
See application file for complete search history.

(56) References Cited

U.S. PATENT DOCUMENTS

| 2,119,484 | A | 5/1938 | Levine |
| 2,179,378 | A | 11/1939 | Metzger |
| 2,207,193 | A | 7/1940 | Groll |
| 2,299,441 | A | 10/1942 | Vaughn |

(Continued)

FOREIGN PATENT DOCUMENTS

| CH | 609022 | 6/1974 |
| CN | 101215220 | 7/2008 |

(Continued)

OTHER PUBLICATIONS

Stevens, "Some New Cyclopropanes with a Note on the Exterior Valence Angles of Cyclopropane", JACS, Vo. 68, No. 4, 1945, 620-622.

(Continued)

*Primary Examiner* — In Suk Bullock
*Assistant Examiner* — Alyssa L Cepluch
(74) *Attorney, Agent, or Firm* — Christopher Logan; KSJLAW, LLC

(57) ABSTRACT

Processes for the production of alkenes are provided. The processes make use of methane as a low cost starting material.

9 Claims, 9 Drawing Sheets

(56) References Cited

U.S. PATENT DOCUMENTS

| | | | |
|---|---|---|---|
| 2,302,228 | A | 11/1942 | Kharasch |
| 2,353,766 | A * | 7/1944 | Schmerling ............ C07C 2/861 570/257 |
| 2,370,342 | A | 2/1945 | Zellner |
| 2,378,859 | A | 6/1945 | Martin |
| 2,435,983 | A | 2/1948 | Schmerling |
| 2,449,286 | A | 9/1948 | Fairbairn |
| 2,588,867 | A | 3/1952 | Elton |
| 2,630,461 | A | 3/1953 | Sachsse et al. |
| 2,688,592 | A | 9/1954 | Skeeters |
| 2,762,611 | A | 9/1956 | Monroe |
| 2,765,359 | A | 10/1956 | Pichler et al. |
| 2,964,579 | A | 12/1960 | Weller et al. |
| 2,973,393 | A | 2/1961 | Monroe |
| 3,000,980 | A | 9/1961 | Asadorian |
| 3,094,567 | A | 6/1963 | Eaker |
| 3,112,988 | A | 12/1963 | Coldren et al. |
| 3,444,263 | A | 5/1969 | Fernald |
| 3,446,859 | A | 5/1969 | Well |
| 3,502,734 | A | 3/1970 | Baird |
| 3,525,595 | A | 8/1970 | Zirngibl et al. |
| 3,551,512 | A | 12/1970 | Loeffler |
| 3,558,438 | A | 1/1971 | Schoenbeck |
| 3,651,019 | A | 3/1972 | Asscher |
| 3,676,508 | A | 7/1972 | Krekeler |
| 3,819,731 | A | 6/1974 | Pitt |
| 3,823,195 | A | 7/1974 | Smith |
| 3,872,664 | A | 3/1975 | Lohmann |
| 3,914,167 | A | 10/1975 | Ivy |
| 3,920,757 | A | 11/1975 | Watson |
| 3,926,758 | A | 12/1975 | Smith |
| 3,948,858 | A | 4/1976 | Wiersum |
| 3,954,410 | A | 5/1976 | Pohl et al. |
| 4,038,372 | A | 7/1977 | Colli |
| 4,046,656 | A | 9/1977 | Davis et al. |
| 4,051,182 | A | 9/1977 | Pitt |
| 4,319,062 | A | 3/1982 | Boozalis et al. |
| 4,513,154 | A | 4/1985 | Kurtz |
| 4,535,194 | A | 8/1985 | Woodard |
| 4,614,572 | A | 9/1986 | Holbrook |
| 4,644,907 | A | 2/1987 | Hunter |
| 4,650,914 | A | 3/1987 | Woodard |
| 4,661,648 | A | 4/1987 | Franklin |
| 4,702,809 | A | 10/1987 | Mueller |
| 4,714,792 | A | 12/1987 | Mueller |
| 4,716,255 | A | 12/1987 | Mueller |
| 4,726,686 | A | 2/1988 | Wolf |
| 4,727,181 | A | 2/1988 | Kruper |
| 4,849,554 | A | 7/1989 | Cresswell et al. |
| 4,894,205 | A | 1/1990 | Westerman |
| 4,902,393 | A | 2/1990 | Mueller |
| 4,999,102 | A | 3/1991 | Cox |
| 5,057,634 | A | 10/1991 | Webster |
| 5,132,473 | A | 7/1992 | Furutaka |
| 5,171,899 | A | 12/1992 | Furutaka |
| 5,178,844 | A | 1/1993 | Carter et al. |
| 5,246,903 | A | 9/1993 | Harley |
| 5,254,771 | A | 10/1993 | Cremer |
| 5,254,772 | A | 10/1993 | Dukat |
| 5,254,788 | A | 10/1993 | Gartside |
| 5,262,575 | A | 11/1993 | Dianis |
| 5,315,044 | A | 5/1994 | Furutaka |
| 5,367,105 | A | 11/1994 | Miyazaki et al. |
| 5,414,166 | A | 5/1995 | Kim |
| 5,504,266 | A | 4/1996 | Tirtowidjojo et al. |
| 5,684,219 | A | 11/1997 | Boyce |
| 5,689,020 | A | 11/1997 | Boyce |
| 5,789,644 | A | 8/1998 | Passler |
| 5,811,605 | A | 9/1998 | Tang |
| 5,895,825 | A | 4/1999 | Elsheikh |
| 5,986,151 | A | 11/1999 | Van Der Puy |
| 6,111,150 | A | 8/2000 | Sakyu |
| 6,118,018 | A | 9/2000 | Savidakis |
| 6,160,187 | A | 12/2000 | Strickler |
| 6,187,976 | B1 | 2/2001 | Van Der Puy |
| 6,229,057 | B1 | 5/2001 | Jackson et al. |
| 6,235,951 | B1 | 5/2001 | Sakyu et al. |
| 6,472,573 | B1 | 10/2002 | Yamamoto |
| 6,518,467 | B2 | 2/2003 | Tung et al. |
| 6,538,167 | B1 | 3/2003 | Brown |
| 6,545,176 | B1 | 4/2003 | Tsay |
| 6,551,469 | B1 | 4/2003 | Nair |
| 6,610,177 | B2 | 8/2003 | Tsay |
| 6,613,127 | B1 | 9/2003 | Galloway |
| 6,683,216 | B1 | 1/2004 | Zoeller |
| 6,825,383 | B1 | 11/2004 | Dewkar |
| 6,924,403 | B2 | 8/2005 | Barnes et al. |
| 6,958,135 | B1 | 10/2005 | Filippi |
| 7,117,934 | B2 | 10/2006 | Lomax |
| 7,189,884 | B2 | 3/2007 | Mukhopadhyay |
| 7,226,567 | B1 | 6/2007 | Olbert |
| 7,282,120 | B2 | 10/2007 | Braun |
| 7,297,814 | B2 | 11/2007 | Yada et al. |
| 7,345,209 | B2 | 3/2008 | Mukhopadhyay |
| 7,371,904 | B2 | 5/2008 | Ma et al. |
| 7,378,559 | B2 | 5/2008 | Verwijs |
| 7,396,965 | B2 | 7/2008 | Mukhopadhyay |
| 7,511,101 | B2 | 3/2009 | Nguyen |
| 7,521,029 | B2 | 4/2009 | Guetlhuber |
| 7,579,510 | B2 * | 8/2009 | Gadewar ............... C07C 1/26 585/310 |
| 7,588,739 | B2 | 9/2009 | Sugiyama |
| 7,659,434 | B2 | 2/2010 | Mukhopadhyay |
| 7,674,939 | B2 | 3/2010 | Mukhopadhyay |
| 7,687,670 | B2 | 3/2010 | Nappa |
| 7,695,695 | B2 | 4/2010 | Shin |
| 7,714,177 | B2 | 5/2010 | Mukhopadhyay |
| 7,794,513 | B2 | 9/2010 | Bartenbach et al. |
| 7,836,941 | B2 | 11/2010 | Song |
| 7,880,040 | B2 | 2/2011 | Mukhopadhyay |
| 7,951,982 | B2 | 5/2011 | Mukhopadhyay |
| 8,058,486 | B2 | 11/2011 | Merkel et al. |
| 8,058,490 | B2 | 11/2011 | Strebelle |
| 8,071,825 | B2 | 12/2011 | Johnson et al. |
| 8,071,826 | B2 | 12/2011 | Van Der Puy |
| 8,076,521 | B2 | 12/2011 | Elsheikh |
| 8,084,653 | B2 | 12/2011 | Tung |
| 8,115,038 | B2 | 2/2012 | Wilson |
| 8,123,398 | B2 | 2/2012 | Teshima |
| 8,158,836 | B2 | 4/2012 | Pigamo |
| 8,232,435 | B2 | 7/2012 | Sievert |
| 8,258,353 | B2 | 9/2012 | Tirtowidjojo |
| 8,258,355 | B2 | 9/2012 | Merkel |
| 8,357,828 | B2 | 1/2013 | Okamoto et al. |
| 8,367,867 | B2 | 2/2013 | Zardi et al. |
| 8,383,867 | B2 | 2/2013 | Mukhopadhyay |
| 8,395,000 | B2 | 3/2013 | Mukhopadhyay |
| 8,398,882 | B2 | 3/2013 | Rao |
| 8,487,146 | B2 | 7/2013 | Wilson |
| 8,558,041 | B2 | 10/2013 | Tirtowidjojo et al. |
| 8,581,011 | B2 | 11/2013 | Tirtowidjojo |
| 8,581,012 | B2 | 11/2013 | Tirtowidjojo |
| 8,614,361 | B2 | 12/2013 | Suzuki |
| 8,614,363 | B2 | 12/2013 | Wilson et al. |
| 8,907,148 | B2 | 12/2014 | Tirtowidjojo et al. |
| 8,926,918 | B2 | 1/2015 | Tirtowidjojo et al. |
| 8,933,280 | B2 | 1/2015 | Tirtowidjojo et al. |
| 8,957,258 | B2 | 2/2015 | Okamoto et al. |
| 9,056,808 | B2 | 6/2015 | Tirtowidjojo et al. |
| 9,067,855 | B2 | 6/2015 | Grandbois et al. |
| 2001/0018962 | A1 | 9/2001 | Joshi et al. |
| 2002/0110711 | A1 | 8/2002 | Boneberg et al. |
| 2006/0150445 | A1 | 7/2006 | Redding |
| 2006/0292046 | A1 | 12/2006 | Fruchey |
| 2007/0197841 | A1 | 8/2007 | Mukhopadhyay |
| 2007/0265368 | A1 | 11/2007 | Rao et al. |
| 2008/0021229 | A1 | 1/2008 | Maughon |
| 2008/0073063 | A1 | 3/2008 | Clavenna et al. |
| 2008/0118018 | A1 | 5/2008 | Schrauwen |
| 2008/0207962 | A1 | 8/2008 | Rao |
| 2009/0018377 | A1 | 1/2009 | Boyce |
| 2009/0088547 | A1 | 4/2009 | Schamschurin et al. |
| 2009/0099396 | A1 | 4/2009 | Mukhopadhyay |
| 2009/0117014 | A1 | 5/2009 | Carpenter |

(56) References Cited

U.S. PATENT DOCUMENTS

| | | |
|---|---|---|
| 2009/0203945 A1 | 8/2009 | Mukhopadhyay |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0087056 A1 | 4/2011 | Tirtowidjojo et al. |
| 2011/0172472 A1 | 7/2011 | Sakyu |
| 2011/0218369 A1 | 9/2011 | Elsheikh et al. |
| 2011/0251425 A1 | 10/2011 | Penzel |
| 2012/0065434 A1 | 3/2012 | Nose et al. |
| 2014/0081055 A1 | 3/2014 | Tirtowidjojo |
| 2014/0163266 A1 | 6/2014 | Tirtowidjojo et al. |
| 2014/0179962 A1 | 6/2014 | Tirtowidjojo et al. |
| 2014/0323775 A1 | 10/2014 | Grandbois et al. |
| 2014/0323776 A1 | 10/2014 | Grandbois et al. |
| 2014/0336425 A1 | 11/2014 | Tirtowdjojo et al. |
| 2014/0336431 A1 | 11/2014 | Tirtowidjojo et al. |
| 2014/0371494 A1 | 12/2014 | Tirtowidjojo et al. |
| 2015/0045592 A1 | 2/2015 | Grandbois et al. |
| 2015/0057471 A1 | 2/2015 | Tirtowidjojo et al. |
| 2015/0217256 A1 | 8/2015 | Tirtowidjojo et al. |

FOREIGN PATENT DOCUMENTS

| | | |
|---|---|---|
| CN | 101492341 | 7/2009 |
| CN | 101544535 | 9/2009 |
| CN | 101597209 | 12/2009 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 0453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54-079207 | 6/1979 |
| JP | S54-135712 | 10/1979 |
| JP | 08-119885 | 5/1996 |
| JP | 2001-151708 | 6/2001 |
| JP | 2001-213820 | 8/2001 |
| JP | 2006-272267 | 10/2006 |
| JP | 2007-021396 | 2/2007 |
| JP | 2008-063314 | 3/2008 |
| JP | 2009-000592 | 1/2009 |
| JP | 2009-046653 | 3/2009 |
| JP | 2011-144148 | 7/2011 |
| LU | 52247 | 12/1966 |
| SU | 899523 | 1/1982 |
| SU | 1122643 | 11/1984 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 12/2012 |
| WO | 2012166393 | 12/2012 |
| WO | 2013082410 | 6/2013 |
| WO | 2014046970 | 3/2014 |
| WO | 2014046977 | 3/2014 |
| WO | 2014066683 | 5/2014 |
| WO | 2014100039 | 6/2014 |
| WO | 2014100066 | 6/2014 |
| WO | 2014134233 | 9/2014 |
| WO | 2014134377 | 9/2014 |
| WO | 2014164368 | 10/2014 |

OTHER PUBLICATIONS

Levanova, et al., "Cholorination of Chloroolefins C3-C4", Doklady Chemistry, vol. 386, No. 4, 2002, 496-498.

Michigan Technological Univ., "Free-Radical Chlorination with Sulfuryl Chloride", Nov. 15, 2001, 1-7.

Ochi, et al., "Preparation of Chloropropenes by Photochemical Dehydrochlorination of 1,2-Dichloropropane", Chemical Abstracts, Jul. 17, 1989, p. 574, 111(3).

Bai et al., "Isomerization of Tetrachloropropene to Promote Utilization Ratio of Triallate Raw Materials" Petrochemical Technology & Application, 2007, 25(1).

Boualy et al., "Kharasch Addition of Tetrachloromethane to Alkenes Catalyzed by Metal Acetylacetonates", Catalysis Communications, 2011, pp. 1295-1297, vol. 12.

Chai et al., "Study of Preparation of 1,1,1,3-tetrachloropropane", Zhejiang Huagong Industry, 2010, pp. 1-3, 41(5).

Cristiano et al., Tetraalkylphosphonium Trihalides. Room Temperature Ionic Liquids as Halogenation Reagents, J. Org. Chem., 2009, pp. 9027-9033, vol. 74.

Evstigneev et al., "Initiated Chlorination of Tetrachloropropane", Khim. Prom., 1984, pp. 393-394, 16(7).

Fields et al "Thermal Isomerization of 1,1-dichlorocyclopropanes", Chemical Communications, Jan. 1, 1967, 1081, No. 21.

Galitzenstein et al., "The Dehydrochlorination of Propylene Dichloride", Journal of the Society of Chemical Industry, 1950, pp. 298-304, vol. 69.

Gault et al., "Chlorination of Chloroform" Comptes Rendus Des Seances De L'Academie des Sciences, 1924, pp. 467-469, vol. 179.

Gerding et al, "Raman Spectra of aliphatic chlorine compounds: chloroethenes an chloropropenes", Recueil Jan. 1, 1955, pp. 957-975, vol. 74.

Hatch et al., "Allylic Chlorides. XV. Preparation and Properties of the 1,2,3Trichloropropenes". JACS, Jan. 5, 1952, pp. 123-126, vol. 74.

Hatch et al., "Allylic Chlorides. XVIII. Preparation and Properties of 1,1,3-tricholoro-2-fluoro-1-propene and 1,1,2,3-tetrachloro-1-propene". JACS, Jul. 5, 1952, pp. 3328-3330, 74(13).

Herzfelder, "Substitution in the Aliphatic Series", Berichte Der Deutschen Chemischen Gesellschaft, 26 (II), May-Aug. 1893, pp. 1257-1261, 26(2).

Ivanov et al., "Metal phthalocyanine-Catalyzed Addition of polychlorine-Containing Organic Compounds to C=C Bonds," Russian Chemical Bulletin, International Edition, Nov. 2009, pp. 2393-2396, 58(11).

Kang et al., Kinetics of Synthesis of 1,1,1,3,3-pentachlorobutane Catalyzed by Fe-FeCl3, Chemical Research and Application, Jun. 2011, pp. 657-660, 23(6).

Kharasch et al., , "Chlorinations with Sulfuryl Chloride.I. The Peroxide-Catalyzed Chlorination of Hydrocarbons", JACS, 1939, pp. 2142-2150, vol. 61.

Khusnutdinov et al., CCl4 Attachment to Olefins Catalyzed by Chromium and Ruthenium Complexes. Impact of Water as a Nucleophilic Admixture, Oil Chemistry, 2009, pp. 349-356, vol. 4.

Kruper et al., "Synthesis of alpha-Halocinnamate Esters via Solvolytic Rearrangement of Trichloroallyl Alcohols", , J Org Chem, 1991, pp. 3323-3329, vol. 56.

Leitch, "Organic Deuterium Compounds: V. The chlorination of propyne and propyne D-4", Canadian Journal of Chemistry, Apr. 1, 1953, pp. 385-386, 30(4).

(56) References Cited

OTHER PUBLICATIONS

Levanova et al.. "Thermocatalytic Reactions of Bromochloropropanes", Russian Journal of Physical Chemistry, Jan. 1, 1983, pp. 1142-1146, vol. 57.

Liu et al., "Progress in Synthesis of 1,1,1,3-tetrachloropropane", Guangzhou Chemicals, 2011, ,pp. 41-42, 39(5).

McBee et al., , Utilization of Polychloropropanes and Hexachloroethane, Industrial and Engineering Chemistry, Feb. 1, 1941, pp. 176-181, 33(2).

Mouneyrat, "Effect of Chlorine on Propyl Chloride in the Presence of Anhydrous Aluminum Chloride" Bulletin de la Societe chimique de france, Societe francaise de chimie, vol. 3, No. 21, Jan. 1, 1899.

Munoz-Molina et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair et al., "Atom transfer radical addition (ATRA) of carbon tetrachloride and chlorinated esters to various olefins catalyzed by CP/Ru(PPh3)(PR3)Cl complexes", Inorganica Chimica Acta, 380 2012, 96-103.

Nguyen et al., "Condensation de chloroforme avec des olefins fluorees en milieu basique," Journal of Fluorine Chemistry, vol. 55, No. 3, Dec. 1, 1991, pp. 241-248.

Nikishin et al, "Reactions of Methanol and Ethanol with Tetrachloroethylene," N. D. Zelinskii Institute of Organic Chemistry, Academy of Sciences of the USSR, 2115-2119. Translated from Izvestiya Akademii Nauk SSSR, Seriya Khimicheskaya 1966, 12, 2188-2192.

Pozdnev et al., "Chlorination of chloroform and the conversion of methylene chloride manufacture still residues", Khim., Khim. Tekhnol. (1970) 70-4.

Rotshtein et al., "Isomer Distribution on Chlorination of Chloropropanes", Z. Organicheskoi Khimii, 2(9), pp. 1539-1542 (1966).

Semenov, "Selectivity of Photochemical Chlorination of Chloromethane in the Liquid Phase", Prikladnei Khimii, vol. 58, No. 4, pp. 840-845 (1985).

Shelton et al., "Addition of Halogens and Halogen Compounds to Allylic Chlorides. I. Addition of Hydrogen Halides," Journal of Organic Chemistry, 23, pp. 1876-1880 (1958).

Skell, et al., "Reactions of BrCl with alkyl radicals", Tetrahedron letters, vol. 27, No. 43, pp. 5181-5184, 1986.

Skell et al., "Selectivities of pi and sigma succinimidyl radicals in substitution and addition reactions, Response to Walling, Wl-Taliawi and Zhao", JACS, vol. 105, No. 15, Jul. 1, 1983, p. 5125-5131.

Tanuma et al., "Partially Fluorinated Metal Oxide Catalysts for a Friedel-Crafts-type Reaction of Dichlorofluoromethane with Tetrafluoroethylene", Catal. Lett. (2010) 136:77-82.

Tobey et al., "Pentachlorocyclopropane 1" Journal of the American Chemical Society, vol. 88, No. 11, Jun. 1, 1996 pp. 2478-2481.

Urry et al., "Free Radical Reactions of Diazomethane with Reactive Bromopolychloroalkane", JACS, vol. 86, No. 9, May 5, 1964, p. 1815-1819.

Wang Chin-Hsien, Elimination Reactions of polyhaloprppanes under emulsion catalytic conditions to give Halopropenes, Synthesis, Teorg Thieme Verlag, Stuttgart, De, vol. 1982, No. 6, Jan. 1, 1982, pp. 494-496.

Zhao et al., "Research Progress on Preparation Technology of 1, 1, 2, 3-Tetrachloropropene," Zhejiang Chemical Industry, vol. 41, No. 6, p. 8-10 (2010).

Zheng et al., "Review of the Preparation of the low GWP alternative 1,3,3,3-tetrafluoropropene", Zhejiang Huagong (2010) 41(3), 5-7.

* cited by examiner

PROCESS FOR THE PRODUCTION OF ALKENES AND/OR AROMATIC COMPOUNDS

FIELD

The present invention relates to the use of methane in the production of alkenes and/or aromatic compounds.

BACKGROUND

The economic viability of any manufacturing business relies, at least to some extent, on the ability to convert low cost starting materials to higher value products. Particularly in the large scale manufacture of commodity chemicals, a difference in material cost of under a dollar per unit, or even pennies per unit, can determine whether a process is economically viable or not. Maximization of the difference between material cost and product value can also render a costly process more economically attractive.

One example of a class of such processes includes processes for the production of higher alkanes and/or alkenes, e.g., those including from three to ten (C3-C10) carbon atoms. Propene, for example, can be used in the production of high performance garments for use by athletes and the military, and is also used in the production of other functional monomers, such as propylene oxide, acrylic acid, allyl chloride, and epichlorohydrin. And, alkanes and alkenes having from three to ten carbon atoms can be used in the production of gasoline.

Many conventional processes for the manufacture of these alkanes and alkenes comprising from three to ten carbon atoms ($C_3$-$C_{10}$), utilize propane as a starting material. Propane may typically cost between twenty and sixty cents per pound. And, processes for the conversion of propane to $C_3$-$C_{10}$ alkanes and alkenes are generally conducted at extreme temperatures, e.g., of 600° C. or greater, and typically require the use of a catalyst. Such process conditions are not only expensive in utility and material cost and capital equipment, but can also generate safety concerns.

Furthermore, gas phase processes conducted at such high temperatures may result in large amounts of reactant, byproduct and/or product decomposition relative to lower temperature processes. Decomposition, in turn, can take the form of carbonaceous deposits forming within the process equipment, which can shorten the time required between reactor cleaning and thereby increase reactor downtime. Catalysts used in high temperature processes may also experience a shortened active lifetime when operated at extreme temperatures, as compared to the lifetimes they may exhibit at lower operating temperatures. While catalyst regeneration is possible, it requires additional capital and operating cost.

Processes for the production of $C_3$-$C_{10}$ alkanes and alkenes would thus desirably be provided that make use of cost effective starting materials. Such processes would be further advantageous if the materials utilized were capable of utilization at operating conditions less intense than conventional materials and/or that require lesser capital expenditure to use. Elimination of the need to employ catalysts would not only provide further material savings, but also capital cost savings via elimination of the need to purchase catalyst regeneration equipment.

BRIEF DESCRIPTION

The present invention provides such processes. More particularly, the present processes utilize a feedstream comprising methane, which is one third the cost of propane, as a starting material. Furthermore, the process does not require the use of solid/heterogeneous catalyst and so capital and operating cost savings are provided. Finally, methane may be converted to alkenes and/or aromatic compounds using lower intensity process conditions than propane, and so, utility and capital cost savings are provided.

In one aspect, there is provided a process for the production of one or more alkenes and/or aromatic compounds, using a feedstream comprising methane. The feedstream is reacted with at least one monochloroalkene, which in some embodiments may be vinyl chloride. The reaction optionally takes place in the presence of a catalyst, such as a free radical initiator. The process is carried out at low process intensity conditions, e.g., temperatures of less than 700° C., or less than 600° C., and pressures of less than 4000 psig, or 3000 psig, or 2000 psig, or 1000 psig, or 500 psig, or 400 psig (2757.9 kilopascals gauge (kPa gauge)), or less than 300 psig (2068.4 kPa gauge), wherein "psig" is used as an abbreviation herein for pounds per square inch gauge. The process may be used to produce $C_3$-$C_{10}$ alkenes and/or $C_5$-$C_{10}$ aromatics. In some embodiments, the process may be used to produce $C_3$-$C_6$ alkenes, and in some of these, may be used to produce propenes, butenes and/or pentenes. The processes may also include the step of converting any alkenes produced, to alkanes, if desired.

Some embodiments of the process may result in the formation of the byproduct HCl, which can then be used to generate the vinyl chloride utilized by the process, by reacting the same with acetylene. The acetylene, in turn, can be generated by partially oxidizing the methane feedstream.

DETAILED DESCRIPTION

Figure 1:
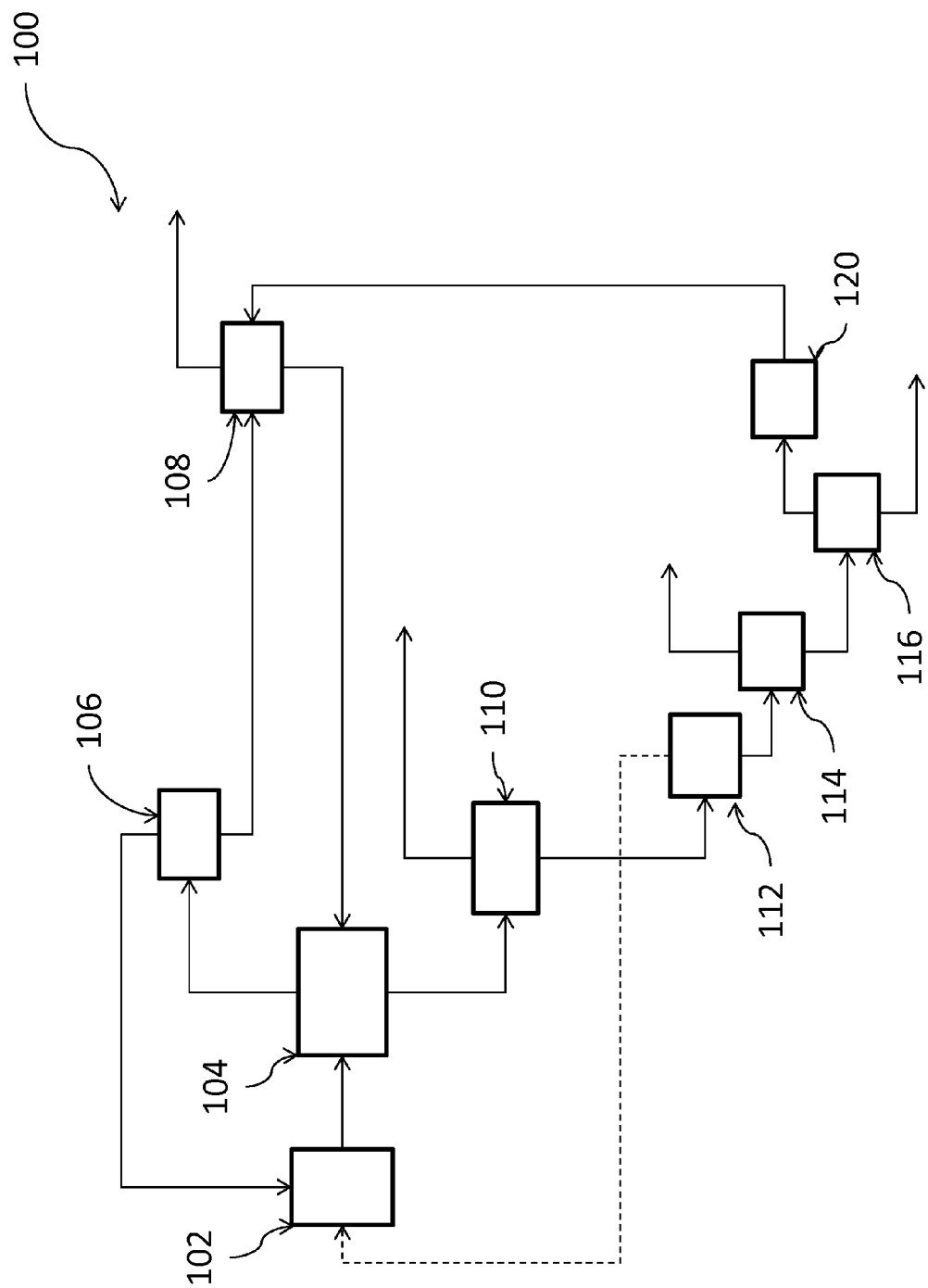
FIG. 1 shows a schematic representation of one embodiment of the process.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

"VCM" may be used herein as an abbreviation for vinyl chloride, "M4" and "CCl4" may be used as abbreviations for carbon tetrachloride, "1,4-Ptd=" may be used as an abbreviation for 1,4-pentadiene. "psig" is used as an abbreviation herein for pounds per square inch gauge, and "kPa" is used as an abbreviation for kilopascals. "CX", wherein X is an integer, is used herein to indicate a molecule having X carbon atoms. An "aromatic" compound, is meant to indicate a compound comprising a conjugated ring of unsaturated bonds, lone pairs of electrons, or empty orbitals, such that the compound exhibits a stabilization stronger than would be expected by the stabilization of conjugation alone.

The present invention provides processes for the production of alkenes and/or aromatics, and in some embodiments, alkenes having from 3 to 10 carbon atoms, or from 3 to 6 carbon atoms and/or aromatic compounds having from 5 to 10 carbon atoms, using a feedstream comprising methane. Methane is a lower cost starting material than, e.g., propane, and furthermore, may be available in some locations via pipeline, thereby avoiding shipping costs. Furthermore, with the proposed process methane may react at lower intensity process conditions that of conventional process using other alkane starting materials. For example, whereas propane often is processed at temperatures of 700° C. or higher, the present processes are conducted at temperatures of less than 700° C., or less than 600° C., or even less than 500° C.

The methane feedstream is desirably reacted with a monochloroalkene having the formula $R_1$—CCl=CH—$R_2$ where $R_1$ and $R_2$ may each independently be hydrogen or an alkyl group having from 1 to 4 carbon atoms. Suitable monochloroalkenes thus include, e.g., vinyl chloride. As mentioned above, the reaction may advantageously take place at temperatures of less than 700° C., less than 600° C. or even less than 500° C. Furthermore, elevated pressures are not required, and in fact, at some level, increased pressure may have little, or no, impact on the conversion of methane and vinyl chloride. And so, pressures of less than 400 psig, or less than 300 psig may be used, if any pressure above ambient is to be used.

The reaction between methane and vinyl chloride will proceed under the stated reaction conditions, but may benefit from being conducted in the presence of a catalyst. In embodiments wherein such advantages are desired, a catalyst may be used. Any free radical catalyst or initiator is believed to be suitable, and those of ordinary skill in the art are aware of many. Any of these may be utilized and examples include, but are not limited to, compounds comprising one or more azo-groups (R—N=N—R') such as azobisisobutyronitrile (AIBN) or 1,1'-azobis(cyclohexanecarbonitrile) (ABCN), organic peroxides such as di-tert-butyl peroxide, benzoyl peroxide, methyl ethyl ketone peroxide, and acetone peroxide. Since the reaction of methane and vinyl chloride is a chain reaction involving chlorine radicals, chlorinated compounds, such as carbon tetrachloride and hexachloroacetone may also be utilized, and in fact, may be preferred. UV or visible light may also be utilized to catalyze chlorinations that proceed via a free radical mechanism. Combinations of any number of these may also be utilized.

The amount of any free radical initiator will depend upon the particular catalyst chosen as well as the other reaction conditions. Generally speaking, in those embodiments of the invention wherein the utilization of a catalyst is desired, enough of the catalyst should be utilized to provide some improvement to reaction process conditions (e.g., a reduction in required temperature) or realized products, but yet not be more than will provide any additional benefit, if only for reasons of economic practicality.

For purposes of illustration only, useful concentrations of each free radical initiator will range from 0.001% to 30% by weight each with respect to vinyl chloride or from 0.01% to 20%, or from 0.1% to 10 wt %, or from 1% to 6 wt %, inclusive of endpoint, intermediate values, and all subranges therebetween. Any endpoint and/or intermediate values are also independently combinable.

The methane and vinyl chloride will react under the described conditions at any molar ratio, and any molar ratio of the two reactants may thus be utilized. Relatively equal molar ratios may be utilized, and a preponderance of one reactant relative to the other is also suitable. And so, in some embodiments, the ratio of methane to vinyl chloride is desirably 1:1, while in others the ratio may desirably be 1:2, or 1:3, or 1:4, or 1:5, or, in other embodiments, may be 2:1, or 3:1, or 4:1, or 5:1. Since vinyl chloride is the limiting reactant in the reaction, excess methane may be present to improve the selectivity to propene and in some embodiments, this may be preferred.

The reaction between methane and vinyl chloride proceeds quickly, and conversion of vinyl chloride, can be seen at the above described reaction conditions in residence times of less than 8 hours, or less than 6 hours, or less than 4 hours, or less than 2 hours, or less than 1 hour, or less than 30 minutes, or less than 15 minutes, or less than 10 minutes, or 5 minutes, or less than 200 seconds, or less than 100 seconds, or less than 50 seconds, or even less than 40 seconds.

When conducted at temperatures of less 700° C., less than 600° C. or even less than 500° C., pressures of less than 4000 psig, or 3000 psig, or 2000 psig, or 1000 psig, or 500 psig, or 400 psig (2757.9 kilopascals gauge (kPa gauge)), or less than 300 psig (2068.4 kPa gauge), and either with or without a free radical catalyst, the reaction of methane with vinyl chloride is expected to produce propene, monochloropropene, 1,4-pentadiene and higher hydrocarbons and aromatics. The selectivity to any particular product may be adjusted by controlling the conversion of vinyl chloride, and in some embodiments, the same is contemplated.

For example, when the production of a greater proportion of pentadienes and aromatic hydrocarbons is desired, the conversion of vinyl chloride is maximized, e.g., to 40% or greater. On the other hand, if lower alkenes, e.g., propenes and monochloropropanes, are desirably produced in greater proportions, the conversion of vinyl chloride may desirably be limited to, e.g., less than 40%. Vinyl chloride conversion may be increased by increasing one or more of reaction temperature, reaction pressure, reactor residence time, and/or the molar ratio of methane to vinyl chloride, while vinyl chloride conversion may be decreased by decreasing one or more of these.

Particular examples of embodiments wherein the vinyl chloride conversion is maximized to increase the production of pentadienes and aromatic hydrocarbons would include processes wherein the molar ratio of methane to vinyl chloride is 3.5, 3.6, 3.7, 3.8, 3.9, 4.0, 4.1, 4.2, 4.3, 4.4, 4.5 or greater, the reaction temperature is 400° C., 440° C., 445° C., 450° C., 455° C., 460° C., 465° C., 470° C., 475° C., 480° C., 485° C., 490° C., 500° C., or greater, reaction pressure is 10, 100, 150, 250, 255, 260, 265, 270, 275, 280, 285, 290, 295, or 300 psig or greater (1723.3, 1757.8, 1792.3, 1826.7, 1861.2, 1895.7, 1930.1, 1964.6, 1999.1, 2033.5, or 2067.9 kPa gauge) and reactor residence time is 0.1, 1, 10, 11, 12, 13, 14, 15, 20, 25, 30, 45 or 60 minutes or longer, wherein each individual parameter is independently combinable with every other individual parameter and subparameter in between.

Particular examples of embodiments wherein the vinyl chloride conversion is limited to increase the production of propenes and monochloropropanes would include processes wherein the molar ratio of methane to vinyl chloride is 3.5, 3.4, 3.3, 3.2, 3.1, 3.0, 2.9, 2.8, 2.7, 2.6, 2.5, or 2.4 or lower, the reaction temperature is 440° C., 435° C., 430° C., 425° C., 420° C., 415° C., 410° C., 405° C., 400° C., 395° C., 390° C., 385° C., or lower, reaction pressure is 4000, 3000, 2000, 1000, 500, 400 300, 250, 245, 240, 235, 230, 225, 220, 215, 210, 205, or 200 psig or lower and reactor residence time is 10, 9, 8, 7, 6, 5, 4, 3, 2, or 1 minute, or 50 seconds, or 40 seconds or less, wherein each individual parameter is independently combinable with every other individual parameter, including endpoints and intermediate values.

A schematic illustration of such a process is shown in FIG. 1. As shown in FIG. 1, process 100 would make use of reactor 102, quench and purification unit 104, separation units 106, 108, 110, 112, 114, and 116, and a dehydrochlorination reactor 120.

In operation, a feedstock comprising methane and vinyl chloride is fed to reactor 102 and reacted at a pressure of from 200 psig to 400 psig and a temperature of from 400° C. to 500° C. to produce to produce monochloropropene, pentadiene, propene, and HCl. This product stream from reactor 102 is provided to a quench and separation unit 104 where the product can be either fully or partially condensed before an overhead stream thereof is fed to separation unit 106.

Separation unit 106 is operated at conditions effective to provide HCl, unreacted methane, and some propene in an overhead stream, recycled to reactor 102, and HCl and propene in a bottom stream that is fed to separation unit 108. Separation unit 108 is operated at conditions effective to provide anhydrous HCl in an overhead stream, and propene and heavier byproducts in a bottoms stream that is recycled to separation unit 104.

The bottom stream from separation unit 104, comprising unreacted vinyl chloride, propene, 1,4-pentadiene and monochloropropene is provided to separation unit 110. Separation unit 110 is operated at conditions effective to provide purified propene in an overhead stream, and vinyl chloride and byproducts in a bottoms stream that is fed to separation unit 112. The overhead of separation unit 112, comprising vinyl chloride, is then recycled to reactor 102, while the bottom stream from separation unit 112, comprising 1,4-pentadiene and monochloropropene, is sent to separation unit 114.

Separation unit 114 provides purified 1,4-pentadiene in an overhead stream, and monochloropropene and heavier byproducts in a bottoms stream. This bottoms stream is provided to a separation unit 116 that provides purified monochloropropene in an overhead stream and heavier byproducts in the bottom stream. The by products are appropriately disposed of, and the monochloropropene isomers are fed to dehydrochlorination reactor 120.

Dehydrochlorination reactor 120 may preferably be a gas-phase reactor operated at temperatures of from 400° C. to 500° C. so that at least a portion of the monochloropropene isomers are converted to propene and HCl. The product stream from dehydrochlorination reactor 120 is recycled to separation unit 108 to recover propene and HCl.

Propenes produced by the present process may typically be processed to provide further downstream products including polypropylene, allyl chloride, acrolein, acrylic acid, and propylene oxide. Since the present invention provides an improved process for the production of propene using a lower cost starting material it is contemplated that the cost savings provided will these downstream processes and/or products. Improved methods for the production of the same are thus also contemplated.

Some embodiments of the invention will now be described in detail in the following examples.

Example 1

Figure 2:
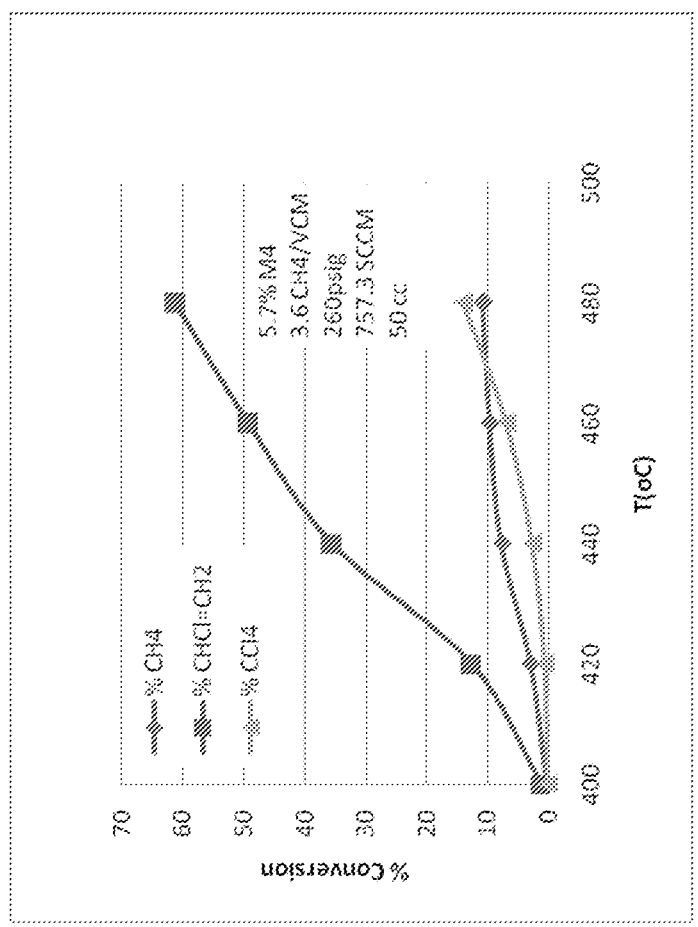
FIG. 2 is a graphical depiction of conversion of methane, vinyl chloride and carbon tetrachloride to monochloropropane, 1,4-pentadiene, and propene as a function of temperature at 260 psig (1792.6 kPa gauge) and a 3.6 molar ratio of methane to vinyl chloride.

A 50 cc reaction tube, having an effective reaction length of 25.34 cm, is isothermally heated to a temperature of 400° C. to 500° C. and charged with a mixture of 3.6 molar ratio of methane to vinyl chloride monomer, with 5.7 mole % carbon tetrachloride as initiator. The residence time is approximately 32 seconds at 260 psig (1792.3 kPa gauge), 420° C. and a flow rate of 757 SCCM. The expected conversion of the limiting reagent, vinyl chloride, is 10%, as shown in FIG. 2. FIG. 2 also shows that higher conversions of the reactants are expected at higher temperatures.

Figure 3:
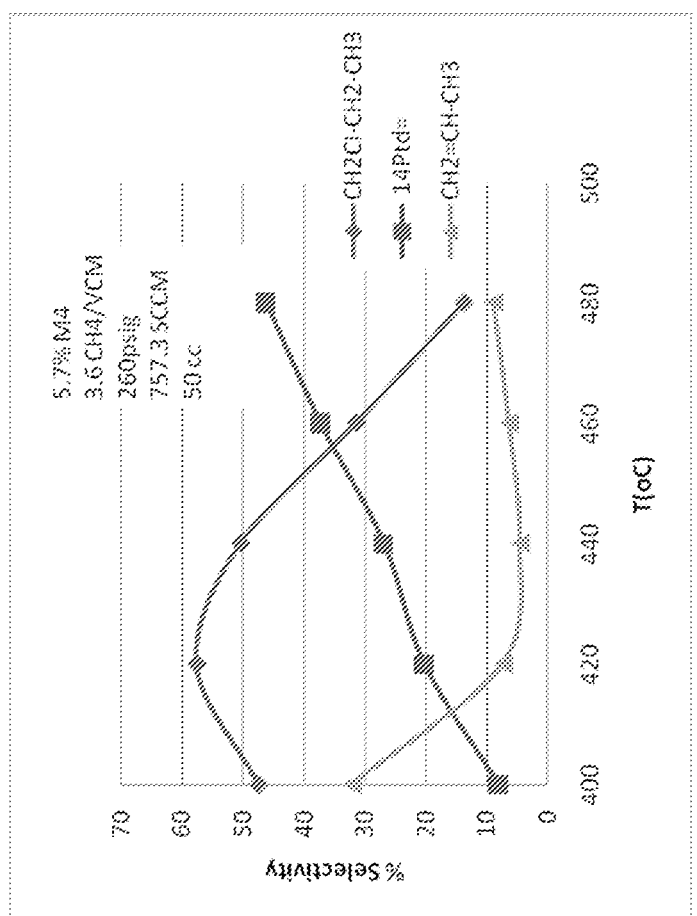
FIG. 3 is a graphical depiction of the selectivity of the reaction of methane, vinyl chloride and carbon tetrachloride to monochloropropane, 1,4-pentadiene, and propene as a function of temperature at 260 psig (1792.6 kPa gauge) and a 3.6 molar ratio of methane to vinyl chloride.

FIG. 3 shows that at temperatures below 440° C. and vinyl chloride conversions of less than 40%, selectivity to propene and monochloropropane is >50%. Here the selectivity is defined as moles of product produced per moles of VCM consumed. Conversions are increased at higher temperatures, as is selectivity to 1,4-pentadiene (14 Ptd=) and other hydrocarbon aromatics. FIG. 3 thus shows that reaction temperature can be used to adjust the relative production rate of propene versus pentadiene and hydrocarbon aromatic compounds.

Example 2

Figure 4:
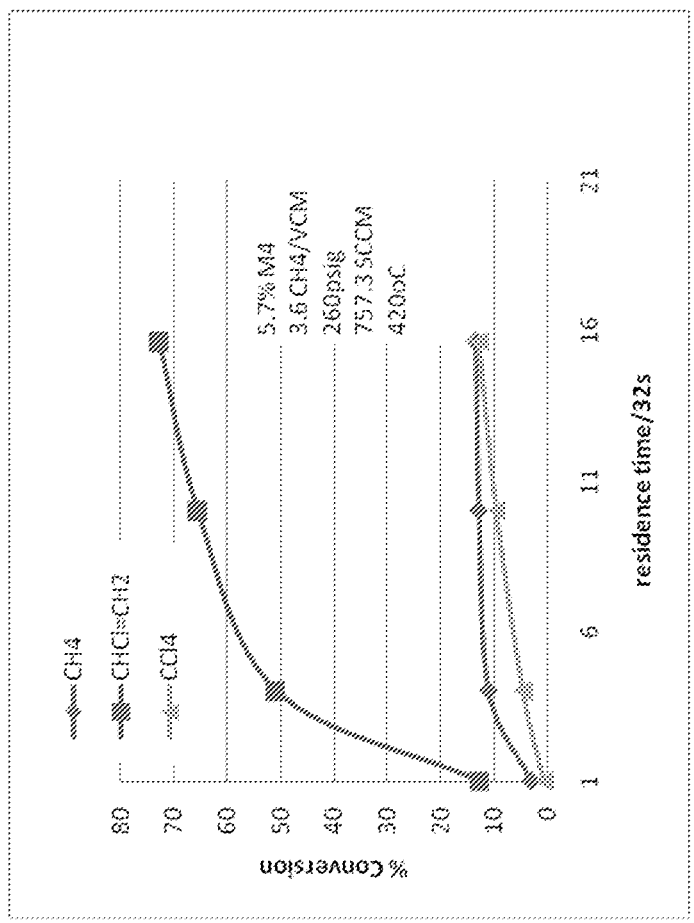
FIG. 4 is a graphical depiction of conversion of methane, vinyl chloride and carbon tetrachloride to monochloropropane, 1,4-pentadiene, and propene as a function of residence time at 260 psig (1792.6 kPa gauge) and a 3.6 molar ratio of methane to vinyl chloride.

A 50 cc reaction tube, having an effective reaction length of 25.34 cm, is isothermally heated to a temperature of 420° C. and charged with a mixture of 3.6 molar ratio of methane to vinyl chloride monomer, with 5.7 mole % carbon tetrachloride as initiator. The residence time is approximately 32 seconds to 8 minutes at 260 psig (1792.3 kPa gauge), 420° C. and a flow rate of 757 SCCM. The expected conversion of the limiting reagent, vinyl chloride, is higher than 40%, as shown in FIG. 4.

Figure 5:
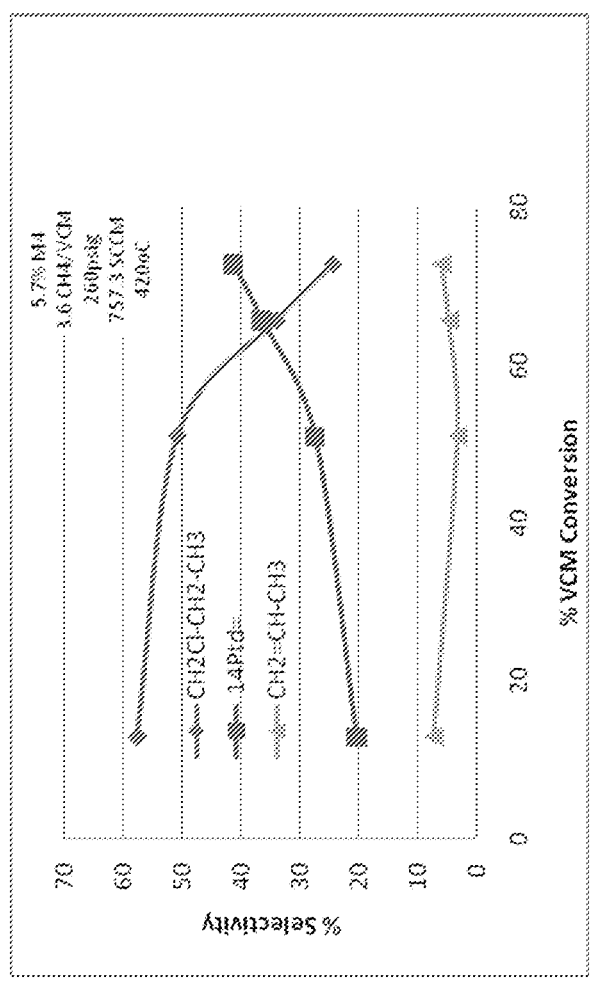
FIG. 5 is a graphical depiction of the selectivity of the reaction of methane, vinyl chloride and carbon tetrachloride to monochloropropane, 1,4-pentadiene, and propene as a function of percent vinyl chloride conversion at 260 psig (1792.6 kPa gauge) and a 3.6 molar ratio of methane to vinyl chloride.

FIG. 5 shows the impact of percent vinyl chloride conversion on product selectivities. FIG. 5 thus shows that residence time can be used to adjust the relative production rate of propene versus pentadiene and hydrocarbon aromatics.

Example 3

Figure 6:
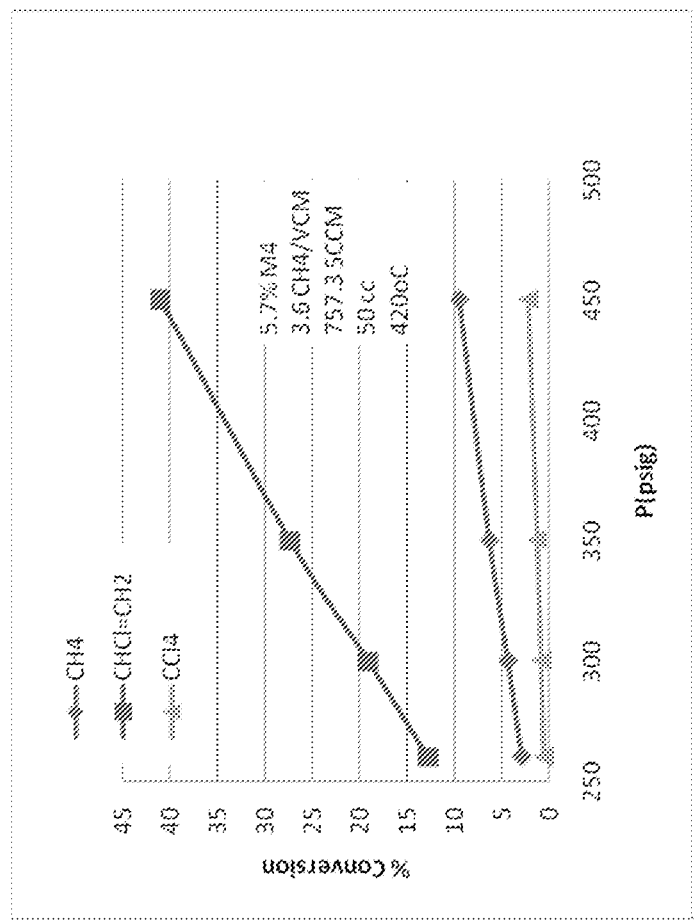
FIG. 6 is a graphical depiction of the conversion of methane, vinyl chloride and carbon tetrachloride to monochloropropane, 1,4-pentadiene, and propene as a function of reactor pressure at 420° C. and a 3.6 molar ratio of methane to vinyl chloride.

A 50 cc reaction tube, having an effective reaction length of 25.34 cm, is isothermally heated to a temperature of 420° C. and charged with a mixture of 3.6 molar ratio of methane to vinyl chloride monomer, with 5.7 mole % carbon tetrachloride as initiator. The pressure is increased from 260 psig (1792.3 kPa gauge) to 450 psig (3102.0 kPa gauge) at a residence time of 32 seconds, 420° C. and a flow rate of 757 SCCM. FIG. 6 shows that reactant conversions are expected to increase with reactor pressure.

Figure 7:
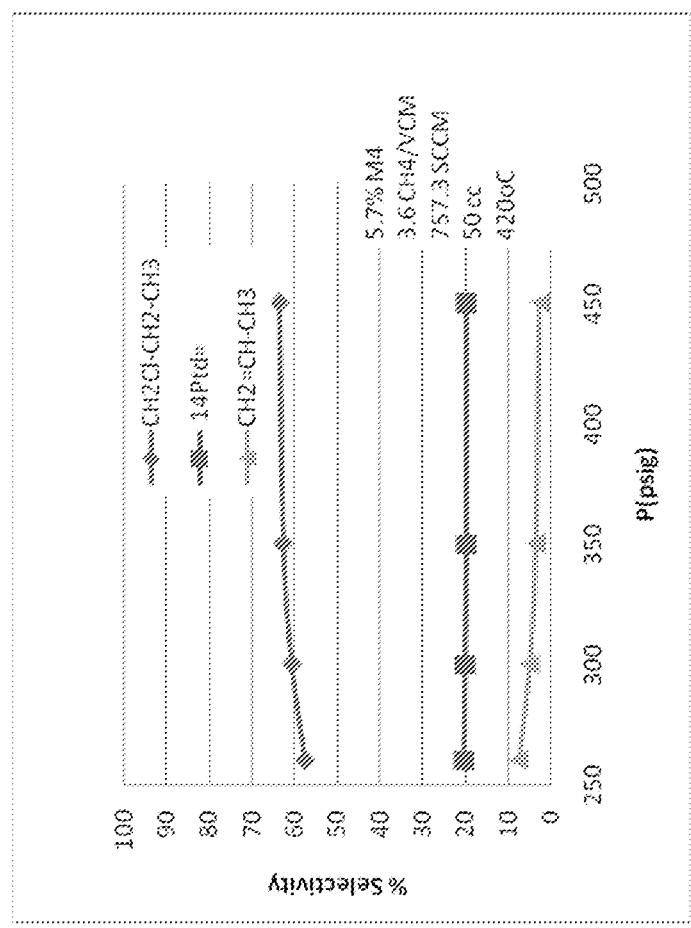
FIG. 7 is a graphical depiction of the selectivity of the reaction of methane, vinyl chloride and carbon tetrachloride to monochloropropane, 1,4-pentadiene, and propene as a function of reactor pressure at 420° C. and a 3.6 molar ratio of methane to vinyl chloride.

FIG. 7 shows that reactor pressure has little impact on product selectivity, so long as the limiting reagent conversion is maintained below 40%.

Example 4

Figure 8:
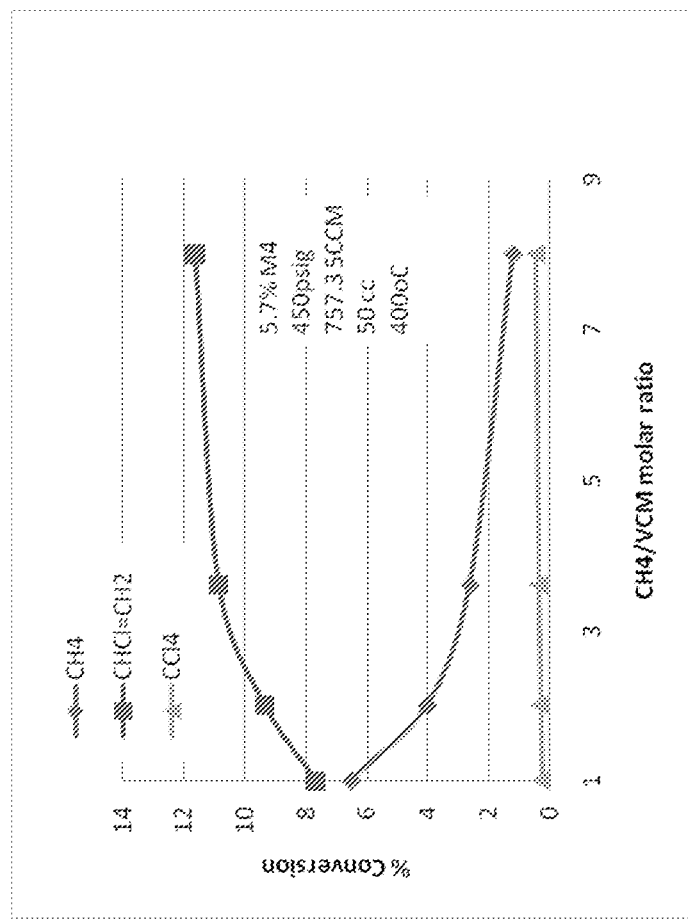
FIG. 8 is a is a graphical depiction of the conversion of methane, vinyl chloride and carbon tetrachloride as a function of the molar ratio of methane to vinyl chloride at 400° C. and 450 psig (3102.6 kPa gauge)

A 50 cc reaction tube, having an effective reaction length of 25.34 cm, is isothermally heated to a temperature of 400° C. and charged with a mixture of from 1:1 to 3.6 molar ratio of methane to vinyl chloride monomer with 5.7 mole % carbon tetrachloride as initiator. The residence time is approximately 32 seconds at 450 psig (3102.0 kPa gauge) and a flow rate of 757 SCCM. FIG. 8 shows the impact of varying carbon tetrachloride vinyl chloride molar ratio at these pressure and temperature conditions.

Figure 9:
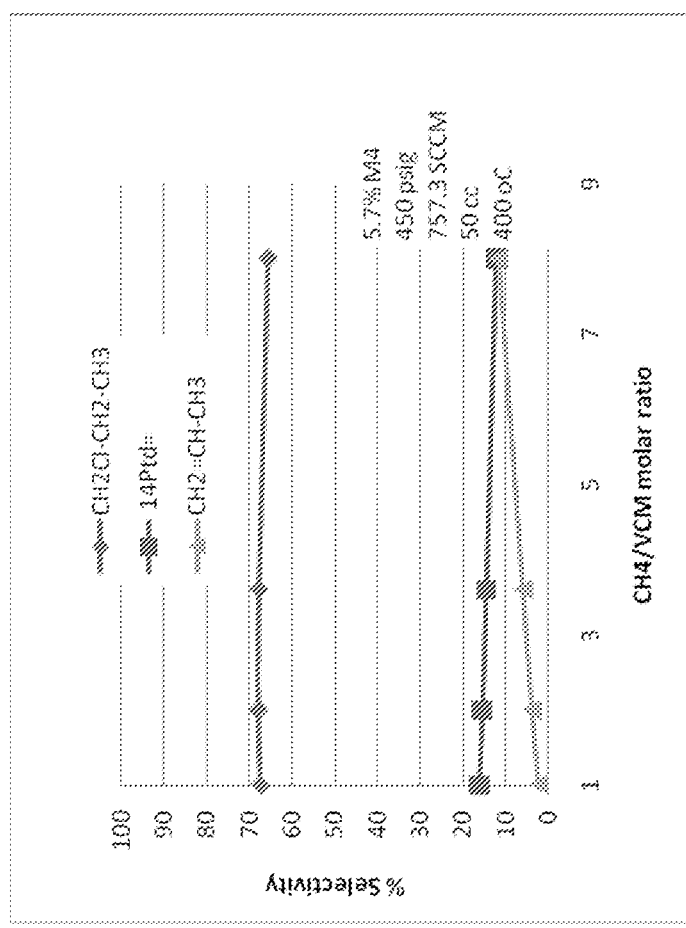
FIG. 9 is a graphical depiction of the selectivity of the reaction of methane, vinyl chloride and carbon tetrachloride to monochloropropane, 1,4-pentadiene, and propene as a function of the molar ratio of methane to vinyl chloride at 400° C. and 450 psig (3102.6 kPa gauge).

FIG. 9 shows that the selectivity to monochloropropene and propene is up to 70% or higher at these conditions, particularly at methane to vinyl chloride molar ratios greater than two.

The invention claimed is:

1. A process for the production of one or more alkenes and/or aromatic compounds, comprising reacting a feedstream comprising methane with at least one monochloroalkene having the formula $R_1$—CCl=CH—$R_2$, where $R_1$ and $R_2$ may each independently be hydrogen or an alkyl group having from 1 to 4 carbon atoms, in the presence of a free radical initiator at a temperature of less than 700° C. and a pressure of less than 4000 psig.

2. The process of claim 1, where the monochloroalkene comprises vinyl chloride.

3. The process of claim 2, wherein the vinyl chloride is generated by reacting acetylene and HCl, wherein the HCl is generated by the process.

4. The process of claim 1, wherein the free radical initiator comprises carbon tetrachloride, hexachloroacetone, hexachloroethane, or combinations of these.

5. The process of claim 1, wherein the one or more alkenes comprise from three to 10 carbon atoms and/or the one or more aromatic compounds comprise from 5 to 10 carbon atoms.

6. The process of claim 5, wherein the one or more alkenes comprise propene and/or 1,4-pentadiene.

7. The process of claim 6, further comprising converting at least one of the one or more alkenes to one or more alkanes.

8. The process of claim 1, wherein at least a portion of the monochloroalkene is generated within, or upstream of, the process.

9. The process of claim 1, wherein the process produces one or more monochloroalkanes comprising from three to 10 carbon atoms.

* * * * *